United States Patent
DiMino et al.

(10) Patent No.: US 10,406,375 B2
(45) Date of Patent: Sep. 10, 2019

(54) APPARATUS FOR APPLYING NITRIC OXIDE TO A TREATMENT SITE

(71) Applicant: ORIGIN INC., Princeton, NJ (US)

(72) Inventors: Andre DiMino, Woodcliff Lake, NJ (US); Matthew Drummer, Fort Lee, NJ (US); Howard Nelson, Lawrenceville, NJ (US); Michael Preston, Orangeburg, NY (US)

(73) Assignee: ORIGIN, INC., Princeton, NJ (US)

( * ) Notice: Subject to any disclaimer, the term of this patent is extended or adjusted under 35 U.S.C. 154(b) by 0 days.

(21) Appl. No.: 15/321,520

(22) PCT Filed: Jun. 23, 2015

(86) PCT No.: PCT/US2015/037179
§ 371 (c)(1),
(2) Date: Dec. 22, 2016

(87) PCT Pub. No.: WO2016/003705
PCT Pub. Date: Jan. 7, 2016

(65) Prior Publication Data
US 2017/0203115 A1    Jul. 20, 2017

Related U.S. Application Data

(60) Provisional application No. 62/019,037, filed on Jun. 30, 2014.

(51) Int. Cl.
*A61N 1/44* (2006.01)
*A61K 33/00* (2006.01)
(Continued)

(52) U.S. Cl.
CPC ............ *A61N 1/44* (2013.01); *A61K 33/00* (2013.01); *A61M 35/003* (2013.01);
(Continued)

(58) Field of Classification Search
CPC ....... A61N 1/44; A61K 33/00; A61M 35/003; A61M 2205/505; A61M 2230/50;
(Continued)

(56) References Cited

U.S. PATENT DOCUMENTS

| 2,415,822 A | 2/1947 | Holmen |
| 2,731,410 A | 1/1956 | Weir |

(Continued)

FOREIGN PATENT DOCUMENTS

| JP | 2006255405 A | 9/2006 |
| RU | 2010580 C1 | 4/1994 |

(Continued)

OTHER PUBLICATIONS

International Search Report and Written Opinion dated Sep. 4, 2015 for PCT application, PCT/US2015/037179 filed Jun. 23, 2015.

(Continued)

*Primary Examiner* — Theodore J Stigell (57) ABSTRACT

A device for generating and delivering Nitric Oxide (NO) to a treatment site includes a main unit, an applicator, a connector hose, and a mobile stand. The main unit provides power and a gas to the applicator via the connector hose. The applicator includes a plasma generator for generating NO in a plasma state. The main unit including a user interface to enable a user to control at least one operational aspect of the device. The applicator includes a pistol grip handle, a trigger for actuating the plasma generator, a hose connection for coupling to the connector hose, and a cowl portion for spacing a tip of the plasma generator at a predetermined distance from a treatment site. Sensors are provided with the applicator for sending feedback and monitoring application site temperature, proximity to the application, applicator motion and the like.

12 Claims, 8 Drawing Sheets

(51) Int. Cl.
*A61M 35/00* (2006.01)
*C01B 21/20* (2006.01)

(52) U.S. Cl.
CPC ....... *C01B 21/203* (2013.01); *A61M 2205/18* (2013.01); *A61M 2205/27* (2013.01); *A61M 2205/3327* (2013.01); *A61M 2205/505* (2013.01); *A61M 2205/584* (2013.01); *A61M 2230/50* (2013.01)

(58) Field of Classification Search
CPC ........ A61M 2205/27; A61M 2205/584; A61M 2205/18; A61M 2205/3327; C01B 21/20; C01B 21/24; C01B 21/203
See application file for complete search history.

(56) References Cited

U.S. PATENT DOCUMENTS

| | | | |
|---|---|---|---|
| 3,169,914 A | 2/1965 | Young et al. | |
| 3,666,408 A | 5/1972 | Grosse et al. | |
| 3,903,891 A | 9/1975 | Brayshaw | |
| 4,010,897 A | 3/1977 | Treharne et al. | |
| 4,287,040 A | 9/1981 | Alamaro | |
| 4,505,795 A | 3/1985 | Alamaro | |
| 4,559,206 A | 12/1985 | Treharne et al. | |
| 4,877,589 A | 10/1989 | O'Hare | |
| 5,396,882 A | 3/1995 | Zapol | |
| 5,843,079 A | 12/1998 | Suslov | |
| 5,950,065 A | 9/1999 | Arlemark | |
| 5,993,612 A | 11/1999 | Rostaing et al. | |
| 6,190,704 B1 | 2/2001 | Murrell | |
| 6,296,827 B1 | 10/2001 | Castor et al. | |
| 6,432,077 B1 | 8/2002 | Stenzler | |
| 6,443,948 B1 | 9/2002 | Suslov | |
| 6,747,062 B2 | 6/2004 | Murrell | |
| 6,749,834 B2 | 6/2004 | Fein et al. | |
| 6,793,644 B2 | 9/2004 | Stenzler | |
| 6,810,288 B2 | 10/2004 | Joshi | |
| 6,955,790 B2 | 10/2005 | Castor et al. | |
| 7,006,874 B2* | 2/2006 | Knowlton | A45D 44/22 607/101 |
| 7,025,869 B2 | 4/2006 | Fine et al. | |
| 7,122,018 B2 | 10/2006 | Stenzler et al. | |
| 7,291,804 B2 | 11/2007 | Suslov | |
| 7,300,436 B2* | 11/2007 | Penny | A61B 18/042 606/34 |
| 7,335,181 B2 | 2/2008 | Miller et al. | |
| 7,361,175 B2 | 4/2008 | Suslov | |
| 7,485,324 B2 | 2/2009 | Miller et al. | |
| 7,498,000 B2 | 3/2009 | Pekshev et al. | |
| 7,520,866 B2 | 4/2009 | Stenzler et al. | |
| 7,589,473 B2 | 9/2009 | Suslov | |
| 7,683,342 B2 | 3/2010 | Morfill et al. | |
| 7,892,198 B2 | 2/2011 | Stenzler | |
| 7,928,338 B2 | 4/2011 | Suslov | |
| 8,030,849 B2 | 10/2011 | Suslov | |
| 8,043,252 B2 | 10/2011 | Miller et al. | |
| 8,105,325 B2 | 1/2012 | Suslov | |
| 8,109,928 B2 | 2/2012 | Suslov | |
| 8,221,800 B2 | 7/2012 | Fine et al. | |
| 8,337,494 B2 | 12/2012 | Suslov | |
| 8,465,487 B2 | 6/2013 | Suslov | |
| 8,613,742 B2 | 12/2013 | Suslov | |
| 8,735,766 B2 | 5/2014 | Suslov | |
| 8,795,222 B2 | 8/2014 | Stenzler et al. | |
| 2003/0028189 A1* | 2/2003 | Woloszko | A61B 18/14 606/45 |
| 2004/0171983 A1* | 9/2004 | Sparks | A61M 5/16827 604/65 |
| 2006/0052772 A1* | 3/2006 | Sartor | A61B 18/042 606/41 |
| 2006/0147553 A1 | 7/2006 | Miller et al. | |
| 2007/0029292 A1 | 2/2007 | Suslov et al. | |
| 2007/0270748 A1* | 11/2007 | Dacquay | A61F 9/0017 604/131 |
| 2009/0012589 A1 | 1/2009 | Watson | |
| 2010/0069851 A1* | 3/2010 | Vad | A61B 17/3401 604/240 |
| 2011/0270121 A1* | 11/2011 | Johnson | A61B 5/0538 600/554 |
| 2012/0022522 A1 | 1/2012 | Suslov | |
| 2013/0172830 A1* | 7/2013 | Hunter | A61F 9/0008 604/295 |
| 2013/0214166 A1* | 8/2013 | Barlow | G01S 5/16 250/342 |
| 2014/0066838 A1* | 3/2014 | Hancock | A61L 2/14 604/23 |
| 2015/0057623 A1* | 2/2015 | Hyde | A61B 5/441 604/290 |

FOREIGN PATENT DOCUMENTS

| | | |
|---|---|---|
| WO | 2011162174 A1 | 12/2011 |
| WO | 2013/052548 | 4/2013 |
| WO | WO-2013/052548 * | 4/2013 |

OTHER PUBLICATIONS

Paulson User Guide; Institute for Testing and Certification; Sep. 29, 2009; pp. 17.

Extended EP Search Report from EP15815265.2, dated Nov. 22, 2017.

* cited by examiner

APPARATUS FOR APPLYING NITRIC OXIDE TO A TREATMENT SITE

CROSS-REFERENCE TO RELATED APPLICATIONS

This is a non-provisional of pending U.S. provisional patent application Ser. No. 62/019,037, filed Jun. 30, 2014, titled "Apparatus for Applying Nitric Oxide to a Treatment Site," the entirety of which provisional application is incorporated by reference herein.

FIELD OF THE DISCLOSURE

The disclosure relates generally to the field of medical treatment and more particularly to an apparatus for effectively administering nitric oxide in the treatment of medical conditions and diseases.

BACKGROUND OF THE DISCLOSURE

Nitric Oxide (NO) gas is a short-lived molecule normally found in a gaseous state both inside and outside the human body. NO is a signaling molecule known to have numerous regulatory, protective and therapeutic properties. Augmenting the body's natural generation of NO by either stimulating increased production of endogenous NO or introducing exogenously-produced NO into the body can improve the body's response to damage, pain, and invading organisms. However, it is difficult to deliver NO into living tissue and, in its gaseous state, NO does not penetrate through the dermis. To be clinically useful, NO must be present in the site of action in a sufficient quantity.

Prior techniques for delivering NO for therapeutic purposes include the administration of chemical compounds which release NO chemically into the body. Other methods employ NO pathway agonists and NO antagonists. Still other methods employ high pressure NO gas and sprays. Yet another method involves surrounding a body with sealed vacuum containers into which gaseous NO is introduced. Attempts have also been made to force pressurized nitric oxide through tissue and skin. For various reasons, these methods have yielded limited results. For example, gaseous NO is highly reactive, has low diffusion constant and has extremely short life-time in tissue media.

Another method that has failed to achieve clinical success involves the administration of molecular donors, which has been demonstrated to be problematic because the control of the release of the payload cannot be modulated, nor can the penetration/saturation of the donors be reliably modulated.

There are several solutions that target specific clinical outcomes involving NO. Sildenafil citrate (sold under the brand name VIAGRA), for example, interferes with the down regulation of NO in erectile dysfunction syndrome. Etanercept (sold under the brand name ENBRIL), for example, uses an anti-TNF alpha antibody to do what NO would do in inflammatory diseases of the joint. Most solutions involve affecting the NO pathways, due to the difficulty in stimulating production of NO directly at the site of action. Because of the lack of site specificity of these NO pathway pharmacologics, negative side effects can be serious.

SUMMARY

In view of the forgoing, it would be advantageous to provide an apparatus and method for administering NO at a site of action in a manner that facilitates therapeutic benefits.

In accordance with the present disclosure, a device for generating and delivering NO to a treatment site is disclosed. The device can include a main unit, an applicator, a connector hose, and a mobile stand. The main unit may provide power and gas to the applicator via the connector hose. The applicator may include a plasma generator for generating Nitric Oxide (NO) in a plasma state. The main unit may include a user interface to enable a user to control at least one operational aspect of the device. The user interface may be a touch screen.

The applicator may include a pistol grip handle, a trigger for actuating the plasma generator, a hose connection for coupling to the connector hose, and a cowl portion for spacing a tip of the plasma generator at a predetermined distance from a treatment site. The cowl portion may include a plurality of ventilation holes along a length of the cowl portion to facilitate cooling of the device.

A safety sensor may be disposed adjacent to a front end of the applicator for providing safety monitoring signals. The safety sensor may comprise a passive infrared skin temperature sensor. The safety sensor may comprise a proximity sensor to enable a user to monitor a distance between the applicator and a treatment area. The proximity sensor may be configured to deactivate the device if the applicator is placed closer than a predetermined distance from the treatment area. The device may include a color illuminator disposed adjacent to a front end of the applicator for projecting a color on the treatment area that is changeable to indicate at least one of a proper use, a warning, and an error. The device may include a motion sensor disposed in or on the applicator, the motion sensor comprising a multi-axis accelerometer for measuring motion of the applicator. The motion sensor can be used to deactivate the device if the applicator is not moved for a sufficient amount of time to prevent over-treating a target site on a patient.

DETAILED DESCRIPTION

The disclosed device will now be described more fully hereinafter with reference to the accompanying drawings, in which various embodiments are shown. The disclosed device, however, may be embodied in many different forms and should not be construed as being limited to the embodiments set forth herein. Rather, these embodiments are provided so that this disclosure will be thorough and complete, and will fully convey the scope of the disclosure to those skilled in the art. In the drawings, like numbers refer to like elements throughout.

In accordance with the present disclosure, a device is disclosed for creating a discrete stream of matter in a plasma state, where the stream has as part of its content NO. In various embodiments the stream can be administered to an organism to obtain a therapeutic result. In some embodiments, NO application at the surface level (i.e., directed at the skin or open wound) is believed to stimulate the body's own production of NO such that therapeutic effects can be obtained at and around the indication site. Alternatively, the disclosed device may exploit the fact that NO in the plasma state is of sufficiently high energy and velocity that it can penetrate through and around cellular membranes. In some cases the NO may pass through biofilms and the stratum corneum to produce therapeutic results in the associated tissue.

Matter in a plasma state that contains NO can be created via several methods. Atmosphere contains nitrogen and oxygen, and thus, sufficient energy in the correct geometry can produce nitric oxide from the gaseous mixture. Energy can be added to transition the gaseous $N_2$ and $O_2$ into the plasma state. In one non-limiting, exemplary embodiment, preformed gaseous in $N_2$—$O_2$ mixture can be created and passed through a plasma energy arc that transfers sufficient energy to production of NO in a plasma state.

Figure 1:
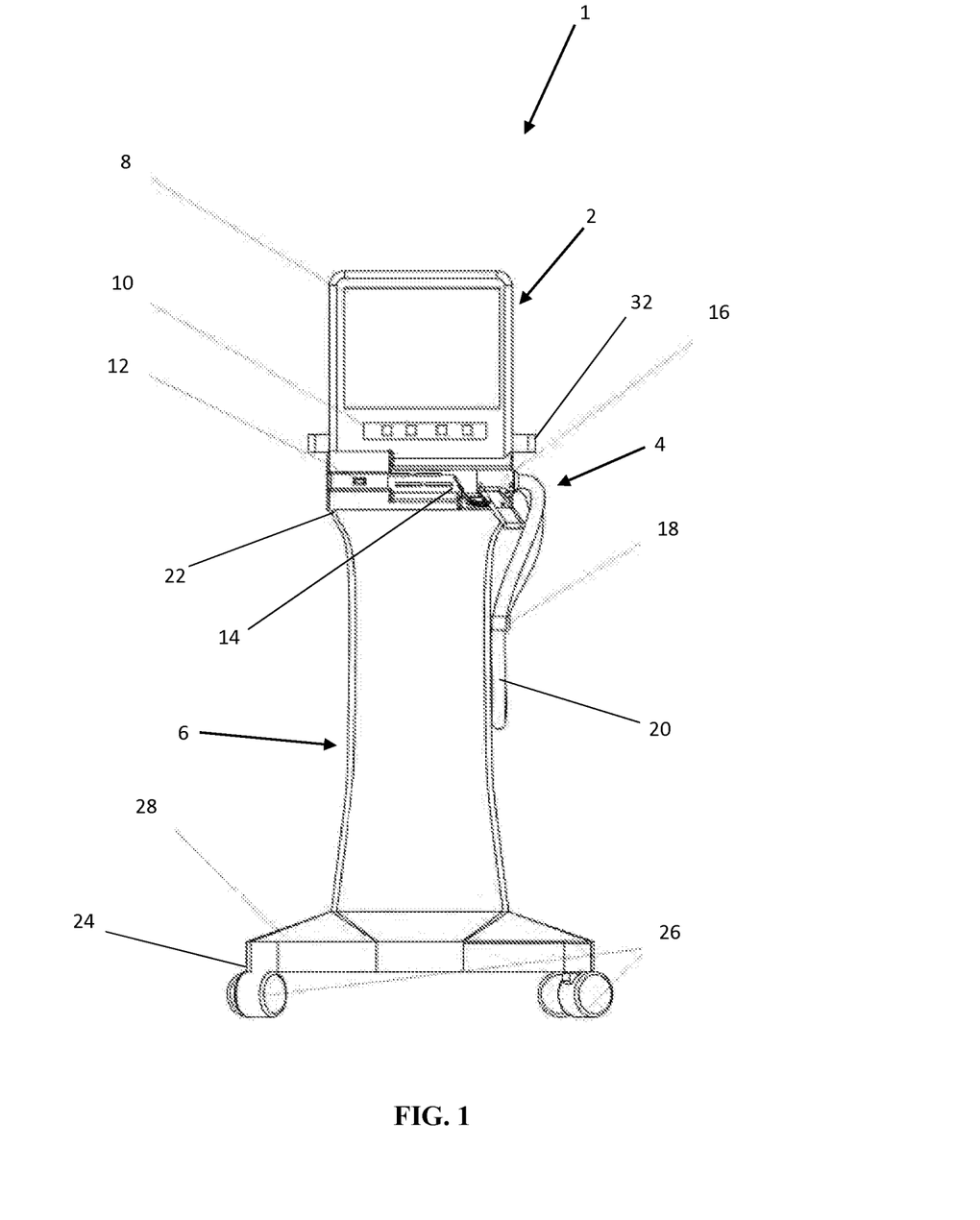
FIG. 1 illustrates an exemplary device for producing NO according to the disclosure.
Figure 2:
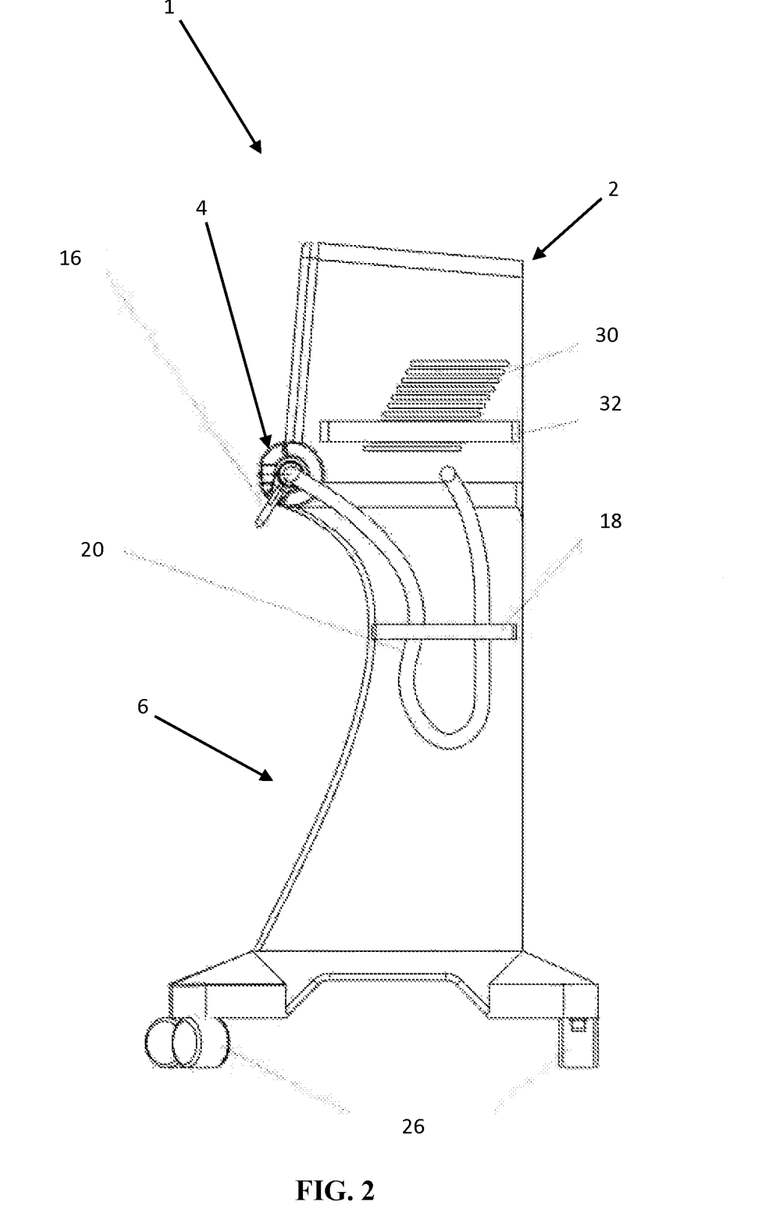
FIG. 2 is a side view of the device of FIG. 1.
Figure 3:
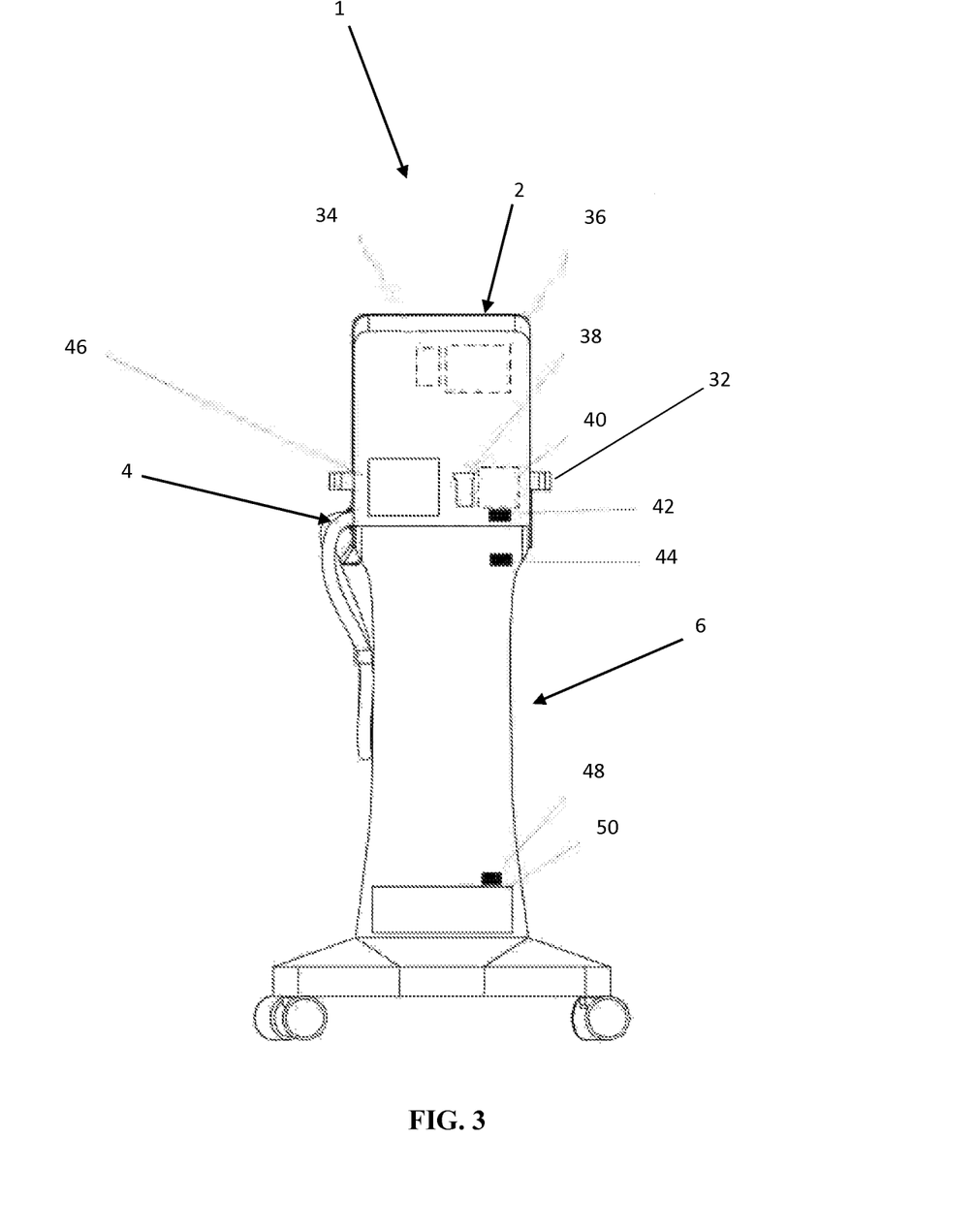
FIG. 3 is a rear view of the device of FIG. 1.

Referring to FIGS. 1-3, a device 1 is shown for generating NO in a plasma state, and for applying such NO to a treatment site. In general, the device 1 can include a main unit 2, an applicator and connector hose assembly 4, and a mobile stand 6. The main unit 2 can include a touch panel display 8, a function button panel 10 and a power control button 12. An applicator housing 14 is positioned on a front side of the main unit 2 to enable easy handling of an applicator 16 of the applicator and connector hose assembly 4. A hose management support 18 may be provided on a side portion of the mobile stand 6 to contain a connector hose 20 of the applicator and connector hose assembly 4 when the device 1 is not in use. The mobile stand 6 may be connected at a first end 22 to the main unit 2. At a second end 24 the mobile stand 6 may include a plurality of wheels 26 to enable the device 1 to be wheeled to a desired location within a treatment facility. The wheels 26 can have a locking feature, and may be disposed within an expanded balanced wheelbase portion 28 to maximize stability of the device 1 as it is being rolled on a floor or other surface.

As can be seen in FIG. 2, the main unit 2 may include appropriate ventilation louvers 30 to maintain the power supply components at a desired operating temperature. A handle 32 can be provided on a side surface of the main unit 2 to allow the device 1 to be moved along a surface via wheels 26.

As shown in FIG. 3, the main unit 2 can include isolated remote communications circuitry and components 34. In some embodiments the remote communications circuitry and components 34 enable communication between the device 1 and a remote computing system (not shown) via any of a variety of appropriate hard-wired communications protocols, including Ethernet, USB host and Client and the like. The main unit 2 can also include one or more wireless remote communications modules 36 to enable wireless communication between the device 1 and a remote computing system via any of a variety of appropriate wireless communications protocols, including WiFi, cellular, Bluetooth and the like.

The main unit 2 further can house a quick change filter housing 38, an internal power supply 40, a power entry module 42, a power output module 44, and a coolant cartridge access panel 46. As will be appreciated, the quick change filter housing 38 and the coolant cartridge access panel 46 may enable easy access to replaceable filter media and coolant cartridges contained in the main unit.

The mobile stand 6 can include a power entry module 48 and an isolated 90-240 VAC 50/60 Hz input 50.

Figure 4:
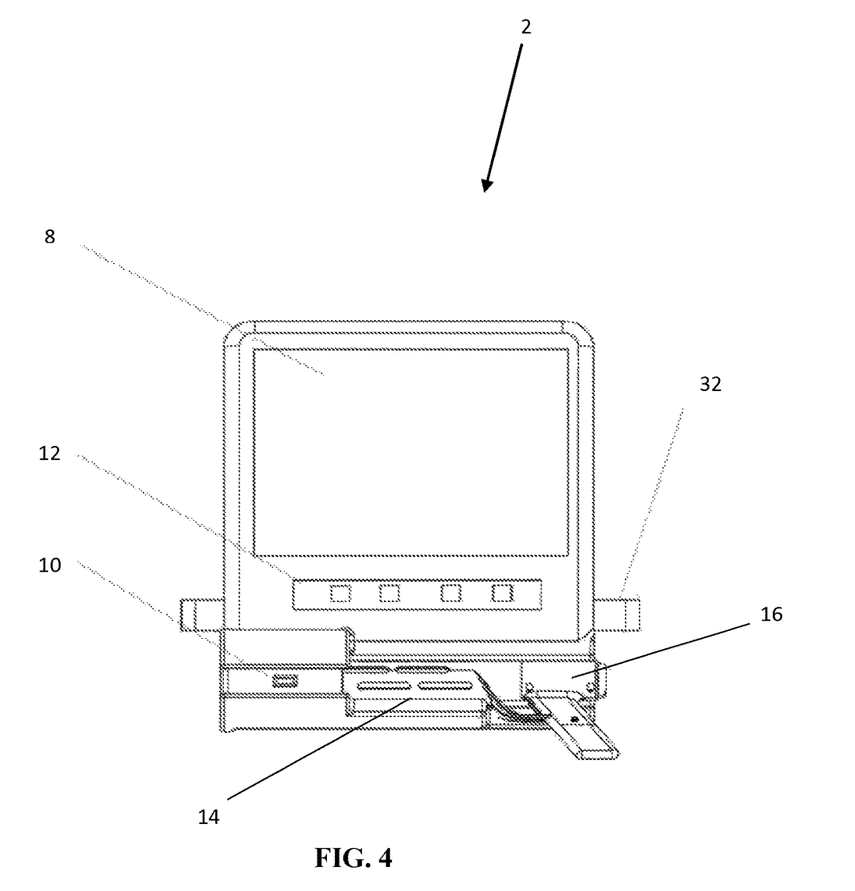
FIG. 4 is a detail view of a portion of the device of FIG. 1.

FIG. 4 shows the main unit 2, which can house the main power systems of the device 1 and can be used to power to the applicator and connector hose assembly 4 by providing air intake, cooling, and electrical power supplies thereto. The main unit 2 can include touch display 8, which in some embodiments can be a color flat panel touch display. The touch display 8 can include a power button 12 and a function button panel 10. To activate the device 1, an operator key code may be entered on the touch display 8 in order to prevent unauthorized usage. As previously noted, applicator housing 14 can be provided on a front side of the main unit 2 to enable easy grasping and re-holstering of the applicator 16 by a user. One or more handles 32 can be disposed on either side of the main unit 2 to allow easy movement of the device 1 on wheels 26.

Figure 5:
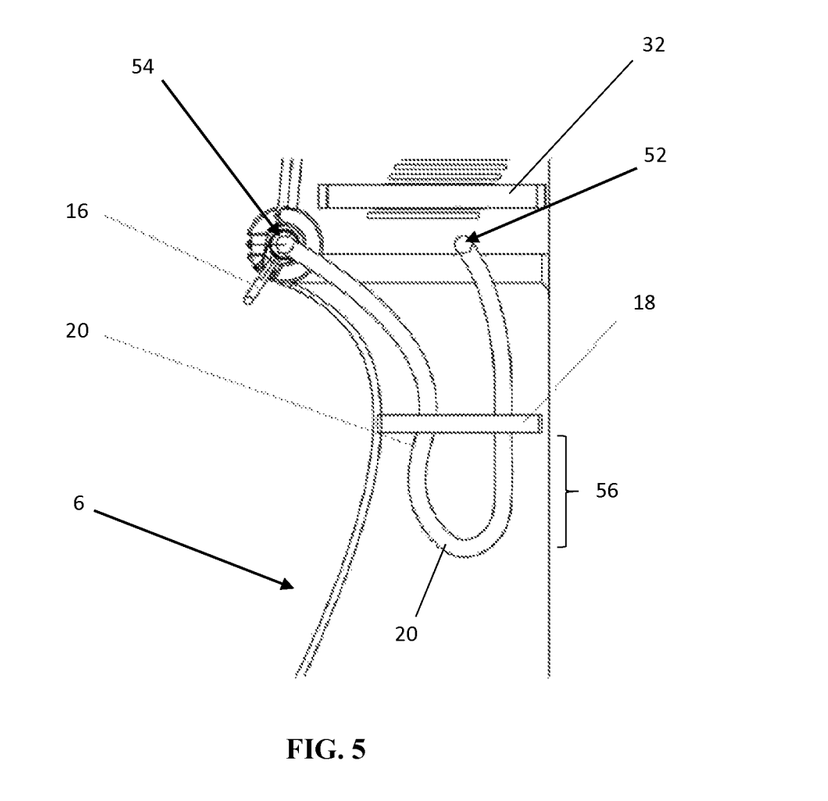
FIG. 5 is a detail view of another portion of the device of FIG. 1.

FIG. 5 shows the applicator and connector hose assembly 4 in which a first end 52 of the connector hose 20 is coupled to the main unit 2 and a second end 54 of the connector hose is coupled to the applicator 16. The connector hose 20 can comprise a flexible tube that connects the applicator 16 to the main unit 2. In some embodiments the connector hose 20 supplies the applicator 16 with a combination of cooling liquid, power, sensor data, and atmospheric air flow that creates a therapeutic action applied with the applicator 16. Hose management support 18 is positioned on a side surface of the mobile stand 6. In the illustrated embodiment this hose management support 18 is a raised bar that is sized and positioned to enable a loop 56 of the connector hose to be captured between the mobile stand 6 and the bar.

Figure 6:
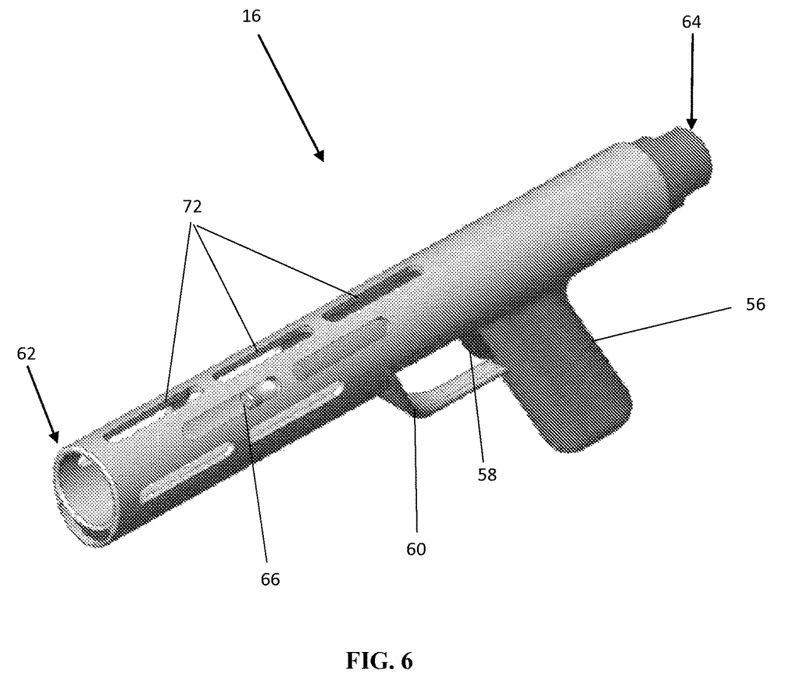
FIG. 6 is an isometric view of an applicator portion of the device of FIG. 1.
Figure 7:
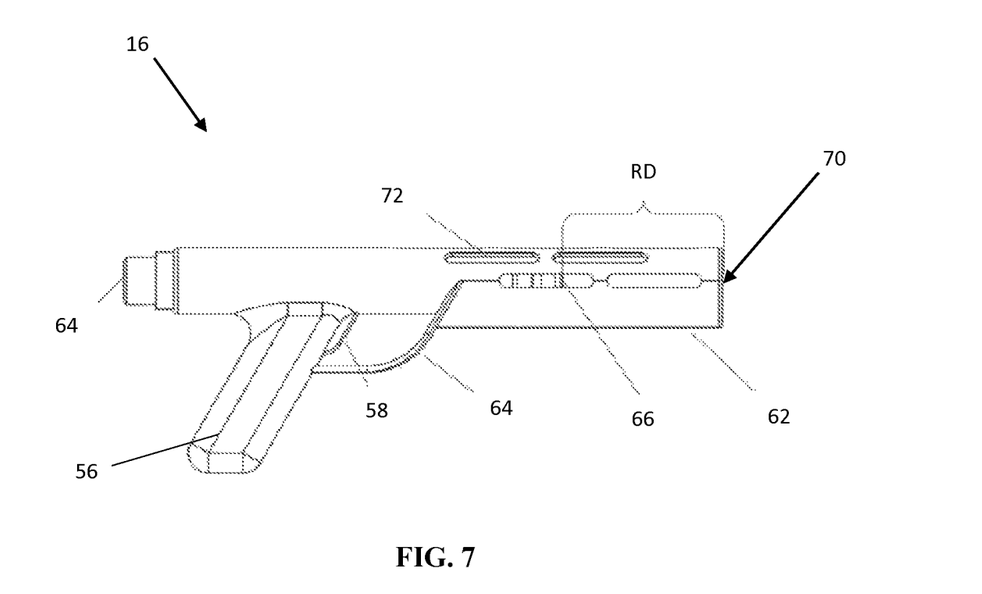
FIG. 7 is a side view of the applicator of FIG. 6.
Figure 8:
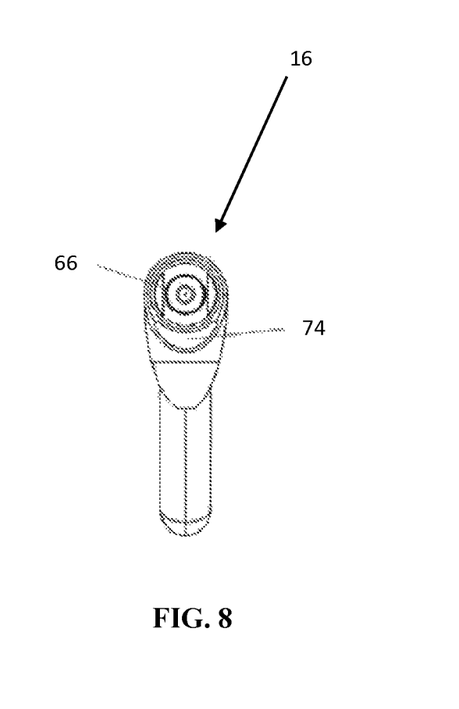
FIG. 8 is an end view of the applicator of FIG. 6.

FIGS. 6-8 shows the applicator 16 in greater detail. The applicator 16 creates NO gas as part of a NO therapy provided by the device 1. As can be seen the applicator 16 comprises a pistol-type arrangement, including a pistol-grip handle portion 56, a trigger portion 58, a trigger guard 60, protective cowl portion 62, and a connection portion 64 for coupling to the second end 54 of the connector hose 20.

As can be seen in FIG. 7, the applicator features a recessed tip 66 within the protective cowl portion 62 which provides automatic distance control during therapy administration. This ensures that the tip 66 of the NO generator portion 68 (FIG. 9) is always held at a desired predetermined offset distance "OD" with respect to the application site. In the illustrated embodiment this predetermined offset distance "OD" is measured from the tip 66 of the plasma generator portion 68 to the front end 70 of the applicator 16.

The protective cowl portion 62 ensures that the NO is provided to a treatment site at a desired temperature, thus eliminating the chance of injury to the user or a patient. The protective cowl portion 62 may include a plurality of ventilation holes 72 along a length thereof to facilitate cooling of the applicator 16 during and after use.

As shown in FIG. 8, a safety sensor and projector array 74 may be provided adjacent to the front end 70 of the applicator 16 to provide a plurality of safety monitoring and alerts. For example, the safety sensor and projector array 74 can include a skin temperature sensor. The skin temperature sensor may include a passive infrared sensor that continually monitors skin surface temperature during therapy to ensure that it remains within a desired predetermined range.

The safety sensor and projector array 74 can also include a proximity sensor that enables a user to determine an optimal distance between the applicator 16 and the treatment area for the safest and most effective therapy. The proximity sensor may deactivate the device if placed too close.

The safety sensor and projector array 74 can also include a color illuminator that projects a color on the treatment area that can change to indicate proper use, warnings, and errors.

The safety sensor and projector array 74 can further include a motion sensor such as a three axis accelerometer. The motion sensor can continually measure the motion of applicator. Should the applicator cease motion for longer than a predetermined amount of time the main unit will deactivate if not moved sufficiently to avoid over-treating a specific target site on a patient.

Each plasma generator portion 68 can be factory tested for NO levels, and calibration data may be included on the plasma generator portion. In some embodiments the plasma generator portion 68 is removable by a user for repair and/or replacement.

Figure 9:
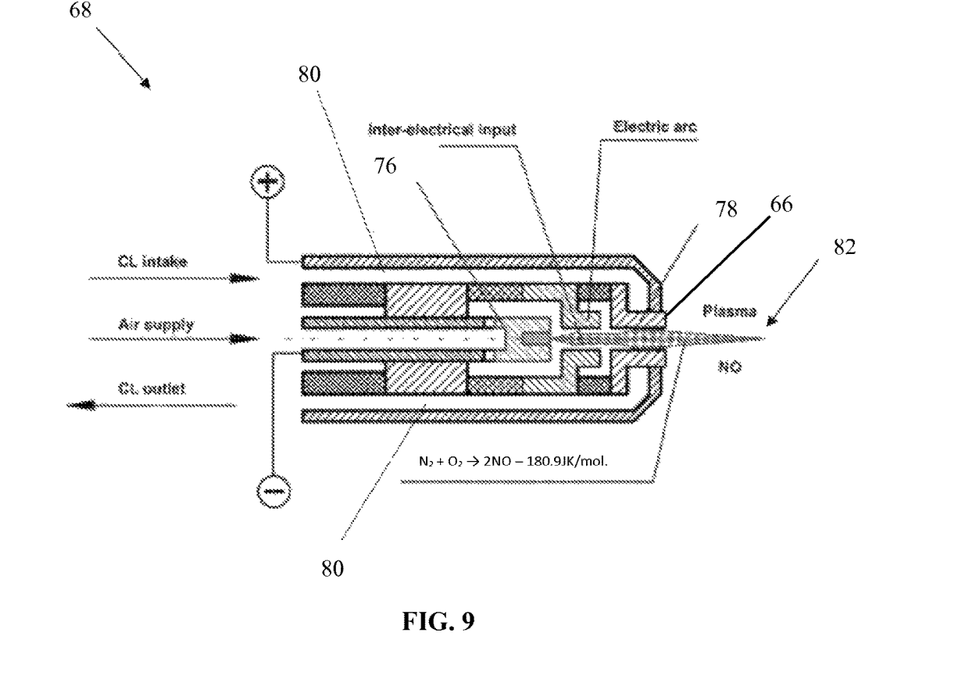
FIG. 9 is a circuit design of a universal generating portion of the applicator of FIG. 6.

FIG. 9 shows an exemplary NO generator portion 68 of the applicator 16. As can be seen, air is introduced at a first end of the generator portion 68, and is channeled between a pair of electrodes, namely a cathode 76 and an anode 78 which are insulated from each other. A stationary DC arc discharge is generated and maintained between the electrodes 76, 78. A NO-containing gas flow is formed from the air in the area between the electrodes 76, 78 under the effect of the arc discharge, and is withdrawn through a cooled channel (cooled by a coolant loop 80), enabling NO to be fixed in the flow 82. The temperature of the flow and the NO content can be brought to desired values for providing a therapeutic benefit to a treatment site. Further details regarding the illustrated exemplary NO generator portion 68 can be found, for example, in U.S. Pat. No. 7,498,000 to Pekshev, the entirety of which is incorporated herein by reference.

Classical thermodynamics confirmed by compositional analysis of the thermodynamical equilibrium of air in a plasma state shows that at a temperature lower than 2000° C. the concentration of NO in the gas does not exceed 1%. Increasing the plasma temperature increases the NO concentration up to its maximum (~5%) at a temperature of 3500-4000° C. Slightly less than 4000° C. is the temperature of the electrical discharge in the plasma arc of the illustrated device 1. Plasma-chemical reactions, which lead to the formation NO, can be expressed by the following chemical formula:

$$N_2 + O_2 \rightarrow 2NO - 180.9 \text{ kilo-Joules per mole (kJ/mol.)}$$

Life-time of the NO molecule at high temperatures is comparable to the time of its synthesis because of fast reaction of recombination ($2NO+O_2=2NO_2$). To prevent recombination and keep therapeutic concentration of NO for medical applications, it is desirable to accomplish rapid cooling of the reaction mixture, i.e., quenching. Quenching of the NO occurs with braking of the escaping flow in surrounding cold air (i.e., from coolant loop 6). The illustrated device 1 enables a direct current plasma arc to be created using ambient air at atmospheric pressure. The device 1 produces a stream of hot air 8 with a composition of plasma species that contains a medically significant amount of NO, which in one exemplary embodiment is about 2,500 parts per million (ppm) NO. In other embodiments the device 1 can produce a stream of hot air 8 with a composition of plasma species that contains up to about 3,500 ppm NO, though that is not limiting and greater concentrations of NO may be provided in further embodiments.

The device 1 shown in FIG. 9 is not exclusive, and alternative sources of plasma-generated NO may also be used with the disclosed applicator 16.

In practice, the NO in a plasma state can be applied directly to or adjacent to living tissue in order to produce the desired effect. It can effectively function to maintain homeostasis in the cardiovascular and respiratory systems. NO, as a signaling molecule, can cause vasodilation which promotes blood vessel flexibility, eases blood pressure, cleans the blood, reverses atherosclerosis and effectively prevents cardiovascular diseases and aids in its recovery. Another important function of NO is slowing down atherosclerotic plaque deposition on vascular walls. NO also plays an active defense role in the immune system. It is a strong antioxidant, and can suppress bacterial infections, viruses and parasitic attacks. It can even deter some types of cancer cell growth. In patients with moderate to severe diabetes, NO can prevent many common and serious complications. NO can also significantly reduce the pain associated with joint swelling in arthritis. NO can effectively decrease the risk of cancer, diabetes, myocardial infarction and stroke.

In the nervous and endocrine systems, NO can induce normal functioning of various body organs. NO can permeate freely through the cell membrane for biological signaling, adjust cellular activities and lead every organ to complete its function properly, including the lungs, liver, kidneys, stomach, heart, brain and genitals. NO can increase blood flow to the genital organs to maintain normal sexual function. The brain transmits signals via its surrounding nerves to the perineal region to provide it with sufficient NO to cause vascular dilation, increasing blood flow to enhance erectile function. Under some conditions, weak erections are the results of insufficient NO production by nerve endings.

NO can also slow the aging process and improve memory. The NO molecules produced by the immune system are not only capable of destroying invading microorganisms, but also help activate and nourish brain cells, significantly slowing aging and improving memory.

As used herein, an element or step recited in the singular and proceeded with the word "a" or "an" should be understood as not excluding plural elements or steps, unless such exclusion is explicitly recited. Furthermore, references to "one embodiment" of the present invention are not intended to be interpreted as excluding the existence of additional embodiments that also incorporate the recited features.

While the present invention has been disclosed with reference to certain embodiments, numerous modifications, alterations and changes to the described embodiments are possible without departing from the sphere and scope of the present invention, as defined in the appended claim(s). Accordingly, it is intended that the present invention not be limited to the described embodiments, but that it has the full scope defined by the language of the following claims, and equivalents thereof.

The invention claimed is:

1. A device for generating and delivering NO to a treatment site, comprising:
    a main unit;
    an applicator;
    a connector hose;
    and a mobile stand;
    wherein the main unit provides power and a gas to the applicator via the connector hose, the applicator including a plasma generator for generating Nitric Oxide (NO), the applicator including a proximity sensor to enable a user to monitor a relative distance between the applicator and the treatment site, and a color illuminator disposed adjacent to a front end of the applicator for providing a color that is changeable to indicate a warning or an error, and wherein the color illuminator is configured for projecting the color on the treatment site that is changeable to indicate the warning or the error.

2. The device of claim 1, the main unit including a user interface to enable the user to control at least one operational aspect of the device.

3. The device of claim 2, the user interface comprising a touch screen.

4. The device of claim 1, the applicator comprising:
a pistol grip handle;
a trigger for actuating the plasma generator;
a hose connection for coupling to the connector hose; and
a cowl portion for spacing a tip of the plasma generator at a predetermined distance from the treatment site.

5. The device of claim 4, the cowl portion including a plurality of ventilation holes along a length of the cowl portion to facilitate cooling of the device.

6. The device of claim 1, further comprising a passive infrared skin temperature sensor to monitor a temperature of the treatment site such that the temperature is maintainable within a predetermined range.

7. The device of claim 1, wherein the proximity sensor is configured to deactivate the device if the applicator is placed closer than a predetermined distance from the treatment site.

8. The device of claim 1, further comprising a motion sensor disposed in or on the applicator, the motion sensor comprising a multi-axis accelerometer for measuring motion of the applicator.

9. The device of claim 8, wherein the motion sensor is configured to deactivate the device if the applicator is not moved sufficiently to prevent over-treating of the treatment site.

10. The device of claim 1, wherein the device is configured to produce a stream of air with a composition of a plasma species that contains a medically significant amount of NO.

11. The device of claim 10, wherein the medically significant amount of NO is 2,500 parts per million (ppm) NO or less.

12. The device of claim 10, wherein the medically significant amount of NO is 3,500 parts per million (ppm) NO or less.

* * * * *